United States Patent [19]
Dufour

[11] 3,983,126
[45] Sept. 28, 1976

[54] ARYLOXY PYRIDINE CARBOXYLIC-4-ACIDS

[76] Inventor: Claude Dufour, 4, Rond-Point Saint James, 92-Neuilly, France

[22] Filed: Apr. 23, 1974

[21] Appl. No.: 463,419

Related U.S. Application Data

[60] Division of Ser. No. 318,651, Dec. 26, 1972, Pat. No. 3,822,278, which is a continuation-in-part of Ser. No. 238,963, March 28, 1972, Pat. No. 3,822,277, which is a continuation of Ser. No. 807,395, March 14, 1969, abandoned.

[30] Foreign Application Priority Data

Dec. 24, 1971 France .............................. 71.46688

[52] U.S. Cl. ............................................. 260/295 R
[51] Int. Cl.² ...................................... C07D 213/02
[58] Field of Search .................. 260/295 R, 295.5 R

[56] References Cited
OTHER PUBLICATIONS

Chemical Abstracts 52: 15529(e) (1958).
Chemical Abstracts 53: P16163(b) 16163 (1959).
Chemical Abstracts 54: 22009(a) (1960).
Chemical Abstracts 55: 21116(a) (1961).

*Primary Examiner*—Norman A. Drezin
*Attorney, Agent, or Firm*—Craig & Antonelli

[57] ABSTRACT

Compounds having the formula:

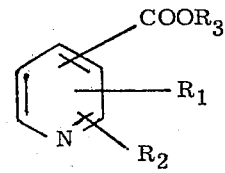

wherein $R_3$ is hydrogen or a lower alkyl group, $R_1$ is chloro, bromo, or fluoro, and $R_2$ is an alkoxy group of 1 to 6 carbon atoms or an aryloxy group which may be substituted with at least one alkyl group or halogen group. These compounds are particularly suitable for the preparation of N-cyclopropyl-pyridyl carboxyl amide derivatives that are useful in the treatment of diseases of the nervous systems in humans and in animals.

3 Claims, No Drawings

ARYLOXY PYRIDINE CARBOXYLIC-4-ACIDS

CROSS-REFERENCE TO RELATED APPLICATIONS

This application is a division of Ser. No. 318,651 filed Dec. 26, 1972, now U.S. Pat. No. 3,822,278, which application is a continuation-in-part of application Ser. No. 238,963 filed on Mar. 28, 1972, now U.S. Pat. No. 3,822,277, which application is a continuation of application Ser. No. 807,395 filed Mar. 14, 1969, now abandoned.

This invention relates to various novel compounds having an amide function and showing particularly interesting pharmacological properties which allow their use in animal or human therapy, and the preparation of these compounds. Heretofore, it has been described in the application Ser. No. 238,963, filed Mar. 28, 1972 (now U.S. Pat. No. 3,822,277), which application is a continuation of application Ser. No. 807,395, filed Mar. 14, 1969 (now abandoned), that compounds having the general formula:

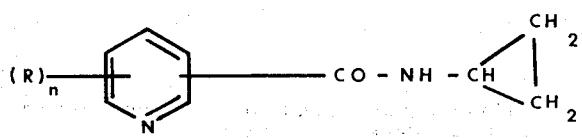

where in $n$ is 0, 1 or 2 and R is one of several members selected from the group consisting of hydrogen and halogen radicals (halogen referring to chlorine, bromine, iodine or fluorine atoms), hydroxy groups (which can be acrylated with carboxylic acids having 1 to 4 carbon atoms), carboxylic acid groups (which can be esterified or amidated), sulfonic acid groups (which can be amidated), and hydrocarbon groups from 1 to 8 carbon atoms which can be branched or cyclic and which may contain one or several multiple-bonds are useful in such therapy. The carboxylic cyclopropylamide group as well as the described substituents R may occupy any of the positions on the pyridine ring. These compounds have particularly interesting properties which allow their use in various applications.

Moreover, it is well known from French Patent No. 1,524,761 of Abbott Laboratories that some amides of 2–6 dichloroisonicotinic acid and particularly N-cyclopropylamide have sedative properties.

In accordance with this invention, particularly interesting properties, for compounds having a general formula similar to that heretofore described have been found wherein R represents two groups, one being a halogen and the other an alkoxy or aryloxy group. These new compounds can be represented by the formula:

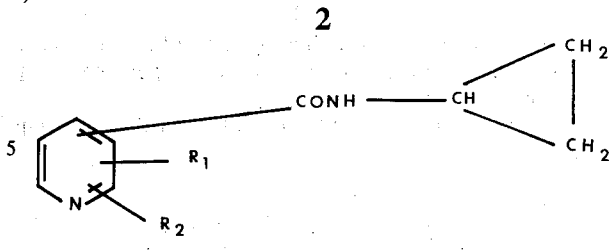

wherein $R_1$ is a halogen group, i.e., a chloro, bromo or fluoro group and $R_2$ is an alkoxy group of 1 to 6 carbon atoms, which may be cyclic, branched or straight chain or an aryloxy group of 6 nuclear carbon atoms constituting a cyclic chain which can be substituted with one or more substituent groups such as the lower alkyl, i.e. methyl, ethyl, and propyl or halogen groups, i.e., chloro, bromo or fluoro or both alkyl and halogen groups. The described carboxylic cyclopropylamide group and the $R_1$ and $R_2$ substituents may occupy any of the positions on the pyridine ring.

The present invention also is concerned with the salts of these new compounds with mineral or organic acids, as well as the addition derivatives thereof through the nitrogen of the pyridine nucleus, such as the halo-alcoholates, the sulfo-alcoholates and the amine oxides.

The present invention also is directed to the preparation of the compounds described hereinabove through the methods described below.

The present invention relates also to the intermediate compounds which can be used to obtain the above-described compounds, as far as these intermediates were not known until now.

The invention is particularly directed to the compounds having an N-cyclopropylcarboxamide group in the 4 position from the nitrogen of the pyridine nucleus and having the substituents $R_1$ and $R_2$ in the 2 and 6 position. These compounds have the following formula:

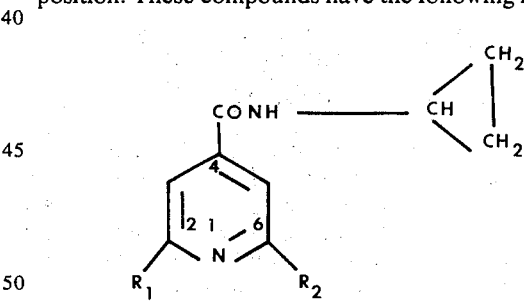

The compounds according to the invention can be prepared from a pyridine-carboxylic acid having already 2 halogen groups and by substituting only one of these groups by the alkoxy or aryloxy group, this substitution being carried out either on the acid itself or on a functional derivative of it.

The carboxylic acid or the functional derivative used are thereafter transformed to an amide function by use of the usual methods of organic synthesis.

As a functional derivative, an ester of the carboxylic acid with an alcohol of low molecular weight may be used. It is also possible in some cases to obtain the required compound with only one reaction from the cyclopropylamide of the dihalogen pyridine carboxylic acid, after substitution of one of the halogen groups by an alkoxy or aryloxy group.

All these reactions can be illustrated by the following formulas:

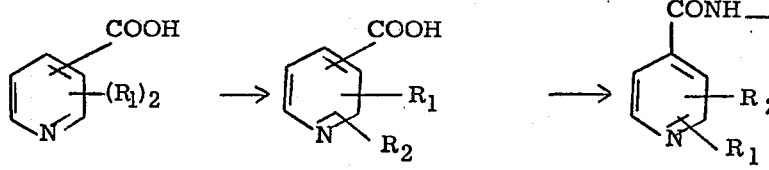 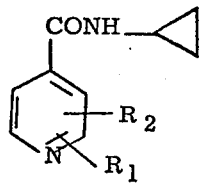

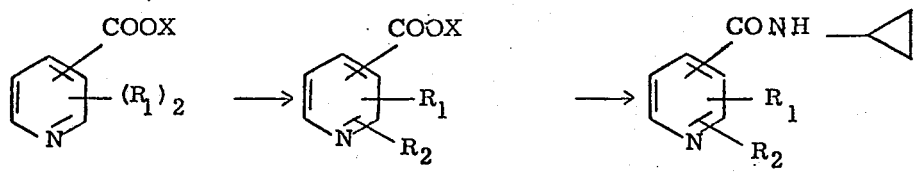 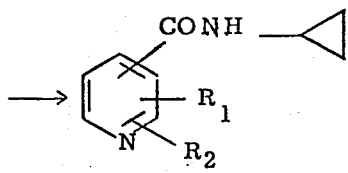

X: alkoyl or alkyl group of low molecular weight, e. g. 1 to 8 carbons.

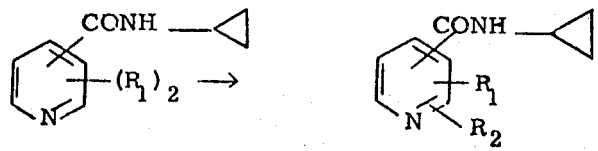

The following examples concerning the preparation of the compounds of the present invention are given merely as illustrative and are not to be considered as limiting, particularly concerning details of reactions such as solvents, temperature, concentration of the reagents, time of reaction, etc.

EXAMPLE 1

Preparation of Chloro-2 Methoxy-6 N-Cyclopropyl-Carboxamido-4 Pyridine a. Preparation of Chloro-2 Methoxy6 Carboxymethyl-4 Pyridine A suspension of 150 gr. of dichloro isonicotinic acid (prepared according to the process described in the Chemical Handbook Houben-Weyl, Volume 5/3, page 925) in 160 ml. of thionyl chloride is heated to reflux during 3 hours. A slight insoluble is filtered. The thionyl chloride in excess is concentrated and the residue is distilled under vacuum.

Obtained in this manner are 108 gr. of 2,6-dichloro isonicotinic acid chloride boiling at 119° to 121°C. under 10 mm. pressure.

This chloride is poured while cooling in excess anhydrous methanol, leading to a clear solution and after some time, the methyl ester crystallizes in the form of white needles with a melting point at 81° C. (Kofler).

100 gr. of methyl ester thus obtained is dissolved in 300 ml. of methanol and stoichiometric quantity of sodium methylate is added thereto.

The reaction mixture is heated to reflux until a neutral reaction is obtained. By concentration of the liquor in vacuo, recovery in water and washing according to the usual methods, the methyl ester of chloro-2 methoxy-6 isonicotinic acid is thus obtained in the form of white crystallized product which melts at 134°C. (Kofler).

The yield reaches 75%. b. N-Cyclopropylamide of Chloro-2 Methoxy-6 Isonicotinic Acid or Chloro-2 Methoxy-6 N-Cyclopropylcarboxamido-4 Pyridine To a suspension of 0.074 mol. of the above compound (a) in 80 ml. of ethylene glycol is added 0.3 mol. of cyclopropylamine. The mixture reaction is stirred at 50°C. for one hour.

Thereafter, everything is passed into solution, then a white solid begins to separate. The mixture is maintained at 50°C. for another 70 hours, then it is cooled and the crystallized product is centrifuged.

The material recrystallized from methanol is obtained as white cottony needles and having melting point at 136°C. (Kofler).

When subjected to the elementary analysis, this product gives the following figures:

C% : 53.15% H% : 5.13% N% : 12.70% Cl% : 15.42%, Calculated for : $C_{10}H_{11}O_2N_2Cl = 226.5$ mol. wt., C% : 52.99% H% : 4.89% N% :12.36% Cl% : 15.64%.

The coincidence of the figures found with the theoretical values establishes with certainty the structure of the new compound.

The product thus obtained, i.e., chloro-2, methoxy-6, N-cyclopropyl carboxamido-4 pyridine is soluble in alcohol at the rate of about 5% and slightly more soluble in acetone and methanol.

It is almost insoluble in water.

EXAMPLE 2

Preparation of N-Cyclopropylamide of Chloro-2 Methoxy-6 Isonicotinic Acid

This product can also be prepared from N-cyclopropylamide of 2,6-dichloro-isonicotinic acid by operating in the following manner:

To a solution of 0.5 gr. sodium (0.0217 mol.) in 20 ml. of methanol is added in one time 5 gr. of 2,6-dichloro-N-cyclopropylisonicotinic amide (prepared by reacting the acid chloride with cyclopropylamine and having a melting point at 149°–151°C. (Microscope).

The mixture is heated to reflux for 30 minutes, then concentrated by half and 200 ml. of water is added.

The white crystal thus prepared are centrifuged and dried and recrystallized in methanol.

The product obtained has a melting point at 134°–136°C. (Kofler) and after mixing it with a sample prepared according to Example 1, the melting point does not show any decrease.

EXAMPLE 3

Preparation of Chloro-2 Phenoxy-6 Cyclopropylcarboxamido-4 Pyridine a. Preparation of Chloro-2 Phenoxy-6 Isonicotinic Acid To the solution of 19.2 gr. (0.1 mol.) of dichloroisonicotinic acid in 80 ml. of dimethyl sulfoxyde is added 11.6 gr. of sodium phenate. The mixture is heated at 130°C. for 10 hours.

After elimination of the solvent under vacuum, recovery of the residue with water and acidification, an oil is separated and recrystallized in isopropyl oxyde.

The chloro-2phenoxy-6 isonicotinic acid is obtained as slightly coloured crystals with a melting point at 167°C. (Kofler).

This acid is refluxed toluene with an excess of thionyl chloride till the end of gas emission. Thereafter, the toluene is concentrated in vacuo, yielding chloro-2 phenoxy-6 isonicotinic acid chloride as a mobile oil.

b. Chloro-2 Phenoxy-6 N-Cyclopropylcarboxamido-4 Pyridine

To a solution of 10 gr. (.0.037 mol.) of the above acid chloride in 50 ml. of dry benzene is added 2.1 gr. (0.037 mol.) of cyclopropylamine.

Everything passes in solution, then a crystallized product separates which is centrifuged, dried and recrystallized in 7 volumes of benzene.

The chloro-2 phenoxy-6 N-cyclopropylcarboxamido-4 pyridine is obtained in the form of white crystal melting at 147°C. (Kofler) and giving the following analytical data:

Cl% : 12.47% N% : 9.84% C% : 61.6% H% : 4.59%, calculated for: $C_{15}H_{13}ClN_2O_2$ = 288.5 mol. wt., Cl% : 12.28% N% : 9.70% C% : 62.4% H% : 4.54%.

EXAMPLE 4

Preparation of Chloro-2 Ethoxy-6 N-Cyclopropyl-Carboxamido -4 Pyridine

By operating as indicated in Example 1, but using sodium ethylate instead of methylate, the chloro-2 ethoxy-6 carboxymethyl-4 pyridine is obtained which can be transformed easily in chloro-2 ethoxy-6 N-cyclopropylcarboxamido-4 pyridine. The product thus obtained is a white crystalline powder melting at 115°C. and giving the following analytical data:

C% : 55.25% H% : 5.35% N% : 11.40% Cl% : 14.9%, Calculated for $C_{11}H_{13}ClN_2O_2$ = 240.68 mol. wt., C% : 54.90% H% : 5.44% N% : 11.63% Cl% : 14.7%.

This compound can also be prepared according to Example 2 by operating in the following manner:

To a solution of 1.5 gr. sodium (0.065 mol.) in 60 ml. of ethanol is added 15 gr. (0.065 mol.) of 2-6 dichloroisonicotinic cyclopropylamide.

The mixture is brought to reflux for 2 hours, and after pouring in 300 ml. of water, the product separates yielding crystals which are centrifuged and recrystallized in methyl ethyl ketone.

The recrystallized product melts at 115°C. (Kofler) as the product prepared with the first method.

EXAMPLE 5

Preparation of Chloro-2 n-Butoxy-6 N-Cyclopropylcarboxamido-4 Pyridine

By operating in an analogous manner to that outlined in Example 4, this compound is easily prepared in the form of white crystals melting at 101°C. after recrystallization in methyl ethyl ketone. Subjected to elementary analysis, it gives the following figures:

C% : 58.30% H% : 6.45% N% : 10.60% Cl% : 13.4%, Calculated for $C_{13}H_{17}ClN_2O_2$ = 268.73 mol. wt., C% : 58.13% H% : 6.52% N% : 10.42% Cl% : 13.18%.

EXAMPLE 6

Preparation of Chloro-2 Iso-Butoxy-6 N-Cyclopropylcarboxamido-4 Pyridine

By operating as above, this compound is obtained in the form of white crystals melting at 129°C.

Subjected to elementary analysis, it gives the following figures:

C% : 57.98% H% : 6.47% N% : 10.65% Cl% : 13.1%, Calculated for $C_{13}H_{17}ClN_2O_2$ = 268.73 mol. wt., C% : 58.13% H% : 6.52% N% : 10.42% Cl% : 13.18%.

EXAMPLE 7

Preparation of Chloro-2 para Chlorophenoxy-6 N-Cyclopropylcarboxamido-4 Pyridine By operating according to the procedure of Example 2, chloro-2 para-chlorophenoxy-6 pyridine carboxylic-4 acid is obtained without difficulty. It has a melting point at 183°–186°C. and may be transformed into acid chloride with thionyl chloride.

By reacting an excess of cyclopropylamine with this acid chloride in toluene and after treatment with the usual processes and recrystallization in ethyl acetate, chloro-2 para-chlorophenoxy-6 N-cyclopropylcarboxamido-4 pyridine is obtained in the form of white needles melting at 190°C. and a yield of 80%.

It gives the following analytical data:

C% : 55.40% H% : 3.80% N% : 8.59% Cl% : 22.14%, Calculated for $C_{15}H_{12}N_2O_2Cl_2$ = 323.18 mol. wt., C% : 55.74% H% : 3.74% N% : 8.67% Cl% : 21.94%.

This product is insoluble in water, soluble in methanol and hot ethanol. By operating in analogous manner the following products have been prepared:

bromo-2 methoxy-6 pyridine carboxylic-4 acid
bromo-2 ethoxy-6 pyridine carboxylic-4 acid
bromo-2 propoxy-6 pyridine carboxylic-4 acid
bromo-2 butoxy-6 pyridine carboxylic-4 acid
as well as the corresponding N-cyclopropylamides:
bromo-2 methoxy-6 N-cyclopropylcarboxamido-4 pyridine
bromo-2 ethoxy-6 N-cyclopropylcarboxamido-4 pyridine
bromo-2 propoxy-6 N-cyclopropylcarboxamido-4 pyridine
bromo-2 butoxy-6 N-cyclopropylcarboxamido-4 pyridine The products, i.e., the N-cyclopropylcarboxamido-containing compounds, of the present invention have a great activity on the central nervous system and a very low toxicity.

These compounds have a LD 50 between 1,000 and 8,000 mg/Kg as measured orally in mice.

In rats, the toxicity observed is slightly, the LD 50 being included between 500 and 2,000 mg/Kg.

In both cases, due to the small solubility of the products, they have been administered orally in oil or aliginate suspensions.

These compounds according to the invention show anticonvulsant effects which result in the inhibition of convulsions and mortality induced by pentylenetetrazol and picrotoxin.

As an example, the following results as obtained in mice with chloro-2 methoxy-6 N-cyclopropylcarboxamido-4 pyridine are given below:

| Doses in oil suspension mg/Kg | % of Survivals | |
|---|---|---|
| | Pentylenetetrazol | Picrotoxin |
| 0 | 0 | 0 |
| 50 | 30 | 20 |
| 75 | 20 | 40 |
| 100 | 70 | 100 |
| 150 | 80 | 90 |
| 200 | | |

The products according to the present invention show equally an hypnotic activity which is manifested by a direct hypnosis at doses from 50 to 250 mg/Kg, as well as by a potentialization of the sleep produced by chloral hydrate and hexobarbital. The central sedatives effects of the products according to the invention have equally been shown by the hole board test of BOISSIER, the rota-rod test, the chimney test and the evasion test. Moreover, the products according to the invention show at various grades analgesic properties.

The present invention also contemplates formation of salts of the compounds described above with all mineral or organic acids, as well as the addition derivatives through the nitrogen atom such as bromo-methylate, iodo-methylate or aminoxyde as well as their use in various industrial and more specially pharmaceutical applications, either separately or in combination with other active principles or excipients and in all pharmaceutical forms such as tablets, cachets, capsules, suppositories, drinkable solutions or injectable preparations for treating all nervous system diseases.

What is claimed is:
1. A compound of the formula:

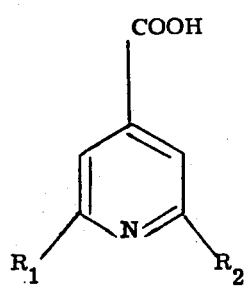

wherein $R_1$ is a chloro, bromo, or fluoro and $R_2$ is an aryloxy group of 6 nuclear carbon atoms which may be substituted with at least one lower alkyl group or halogen group.

2. Chloro-2 phenoxy-6 isonicotinic acid.
3. Chloro-2 para-chlorophenoxy-6 pyridine carboxylic-4 acid.

* * * * *